US005111855A

United States Patent [19]

Boeck et al.

[11] Patent Number: 5,111,855

[45] Date of Patent: May 12, 1992

[54] PLANT AND APPARATUS FOR PRODUCING PERFUMES

[75] Inventors: Alexander Boeck, Duesseldorf; Eckhard Niebaum, Moers; Walter Sommer, Krefeld; Guenter Sparenberg, Ratingen, all of Fed. Rep. of Germany

[73] Assignee: Henkel Kommanditgesellschaft auf Aktien, Duesseldorf-Holthausen, Fed. Rep. of Germany

[21] Appl. No.: 647,181

[22] Filed: Jan. 24, 1991

Related U.S. Application Data

[63] Continuation of Ser. No. 383,394, Jul. 20, 1989, abandoned.

[30] Foreign Application Priority Data

Jul. 21, 1988 [DE] Fed. Rep. of Germany ....... 3824727

[51] Int. Cl.[5] ........................ B01F 15/04; B01F 15/02; G01F 11/00; A61K 7/00

[52] U.S. Cl. ...................................... 141/83; 141/103; 141/104; 141/157; 141/170; 141/144; 177/70; 222/132

[58] Field of Search ................. 141/83, 100, 103, 104, 141/157, 129, 156, 159, 160, 168, 170–172, 144, 234, 236, 351, 360, 361; 177/70, 54, 55, 58; 222/56, 77, 129, 132, 144, 135, 144.5

[56] References Cited

U.S. PATENT DOCUMENTS

| | | | |
|---|---|---|---|
| 2,515,412 | 7/1950 | Lee | 177/54 X |
| 2,781,995 | 2/1957 | Magnuson et al. | 177/54 |
| 2,979,233 | 4/1961 | Smith | 222/135 |
| 3,103,960 | 9/1963 | Simjian | 141/351 |
| 3,105,525 | 10/1963 | Boucher | 141/101 |
| 3,134,509 | 5/1964 | Heiss et al. | 222/135 |
| 3,145,741 | 8/1964 | Smith | 141/104 |
| 3,326,530 | 6/1967 | Schlernitzauer | 366/144 |
| 3,333,648 | 8/1967 | Dodd | 177/55 |
| 3,777,937 | 12/1973 | Buck | 222/399 |
| 3,827,467 | 8/1974 | Henley et al. | 141/104 |
| 3,851,798 | 12/1974 | Miller | 222/135 |
| 3,878,907 | 4/1975 | Morick | 177/70 |
| 4,046,287 | 9/1977 | Hoekstra et al. | 141/329 |
| 4,230,195 | 10/1980 | Graffin | 177/54 X |
| 4,258,759 | 3/1981 | Achen | 141/100 |
| 4,522,274 | 6/1985 | Konishi et al. | 177/70 X |
| 4,526,215 | 7/1985 | Harrison et al. | 141/83 |
| 4,549,674 | 10/1985 | Alticosalian | 222/48 |
| 4,585,148 | 4/1986 | Ito | 141/83 |
| 4,588,001 | 5/1986 | Leonard | 141/145 |
| 4,614,018 | 9/1986 | Krall | 29/33 J |
| 4,621,664 | 11/1986 | Pryor et al. | 141/100 |
| 4,656,463 | 4/1987 | Anders et al. | 340/521 |
| 4,676,282 | 6/1987 | Bellini et al. | 141/83 |
| 4,705,083 | 11/1987 | Rossetti | 141/83 |
| 4,849,175 | 7/1989 | Dupain et al. | 177/52 X |
| 4,913,198 | 4/1990 | Hayahara et al. | 141/103 X |
| 4,928,473 | 5/1990 | Nagao et al. | 177/58 X |
| 4,944,337 | 7/1990 | Credle, Jr. et al. | 141/103 X |
| 4,967,938 | 11/1990 | Hellenberg | 222/144 |
| 4,972,882 | 11/1990 | Kohashi | 177/55 X |

FOREIGN PATENT DOCUMENTS

| | | | |
|---|---|---|---|
| 0808384 | 7/1951 | Fed. Rep. of Germany | 177/70 |
| 1110569 | 2/1956 | France . | |
| 2245496 | 4/1975 | France . | |
| 2582912 | 12/1986 | France . | |
| 64-09102 | 1/1989 | Japan | 141/156 |
| 02-04604 | 1/1990 | Japan | 141/83 |
| WO86/02320 | 4/1986 | World Int. Prop. O. . | |

*Primary Examiner*—Ernest G. Cusick
*Assistant Examiner*—Casey Jacyna
*Attorney, Agent, or Firm*—Wayne C. Jaeschke; Kenneth Watov; Daniel S. Ortiz

[57] ABSTRACT

An automated perfume processing plant for dosing and mixing different substances for the production of perfumes, includes a plurality of reservoirs for different substances, a plurality of outlet dosing valves controlled by a control computer individually arranged on each reservoir, respectively, above a line of mixing vessels on a conveyor belt, whereby the computer is programmed for responding to a perfume code signal from a scanner scanning codes imprinted on each moving vessel, for operating the conveyor belt and dosing valves to deposit a given amount of selected ones of the substances in the mixing vessels for obtaining a desired perfume formulation in each vessel.

5 Claims, 2 Drawing Sheets

PLANT AND APPARATUS FOR PRODUCING PERFUMES

This application is a continuation of application Ser. No. 383,394, filed Jul. 20, 1989 now abandoned.

BACKGROUND

1. Field of the Invention

This invention relates generally to a plant for dosing and mixing different substances, and more particularly to apparatus for the production of perfumes.

2. Discussion of Related Art

In preparing and developing certain perfume formulations, individual perfumes have to be mixed together in exact doses, particularly for test purposes. The individual perfumes are stored separately from one another in reservoirs or the like. To prepare a perfume mixture, the particular perfumes required are taken manually from the individual reservoirs. The individual quantity for each perfume can be determined by weighing or by using a corresponding measuring cup. The desired perfume is then prepared by mixing the individual perfumes in a mixing vessel.

However, this procedure is very complicated because one operator is required for the preparation of each mixture. The individual components must be laboriously blended together by weighing or the like. Human errors may occur due to inaccurate dosing or even incorrect dosing.

3. Summary of the Invention

With the problems in the prior art in mind, the present invention provides a solution which enables different substances, particularly liquids, to be accurately dosed and mixed without error, in an automated processing plant, in the absence of an operator.

According to the invention, this problem is solved by a plant including apparatus comprising an outlet dosing valve controlled by a control computer arranged on each reservoir above a line of mixing vessels, in combination with a mixing vessel designed to travel along the line of mixing vessels associated with each outlet dosing valve under computer control.

With a fully automatic plant designed in this way, any desired mixture can be prepared from substances contained in the reservoirs associated with the plant in the absence of operators. The necessary data, such as quantity and composition for the particular mixture, are fed into the control computer. Under the control of the control computer, a mixing vessel is brought, in successive order, beneath the corresponding outlet dosing valves of the reservoirs and filled with the particular quantity necessary by means of the outlet dosing valve (controlled by the computer) of the associated reservoir.

In one embodiment of the invention, an inert gas (nitrogen, for example) is fed under variable pressure to the reservoirs. This inert gas cushion in the reservoirs guarantees constant pressure conditions at the dosing valves, for providing reliable control of the particular quantities released.

It is of particular advantage in this regard for the mixing vessel to be arranged on a weighing unit connected to the control computer. In this manner, possible sources of error can be eliminated during dosing, because the particular quantity to be released from a particular reservoir is determined both by measurement of the throughflow volume at the outlet dosing valve, and by monitoring of the quantity released by the weighing unit. In addition, the consumptions of the various perfumes can be balanced by the weighing unit connected to the control computer.

To enable several mixtures to be automatically prepared continuously and successively in the plant or perfume factory according to the invention, the line of mixing vessels is preceded by a store of mixing vessels with a conveyor belt.

In another embodiment of the invention, a handling unit is arranged between the line of mixing vessels and the store of mixing vessels to transfer the mixing vessels from the store to the line. This embodiment is intended for cases where the conveyor belt of the store is not directly coupled with the line of mixing vessels.

In one particularly practical embodiment of the invention, each mixing vessel is provided with a code designed to be read by a scanner arranged at the end of the store of mixing vessels and connected to the control computer. In this way, the data of a perfume mixture can be read off by the control computer through coded formulation numbers. Individual mixture formulations may be fed into the computer through a terminal or, alternatively, computer-controlled series mixtures may even be prepared.

In one particularly preferred embodiment of the invention, the line of mixing vessels is in the form of a turntable with a weighing unit designed to travel in a circle. The dosing valves are preferably arranged in a circle with the radius of the weighing unit. This arrangement of the individual elements of the plant is particularly space-saving.

To obtain an even more compact arrangement, several dosing valves may be arranged together in groups.

Finally, in another embodiment of the invention, another store of mixing vessels with a conveyor belt is arranged at the end of the line of mixing vessels. An arrangement such as this is of advantage when mixtures are to be stored rather than used immediately, i.e. a whole series of mixtures can be prepared overnight, for example.

BRIEF DESCRIPTION OF THE DRAWINGS

The invention is described by way of example in the following with reference to the accompanying drawings, in which like items are indicated by the same reference designation, wherein.

DETAILED DESCRIPTION OF THE INVENTION

Figure 1:
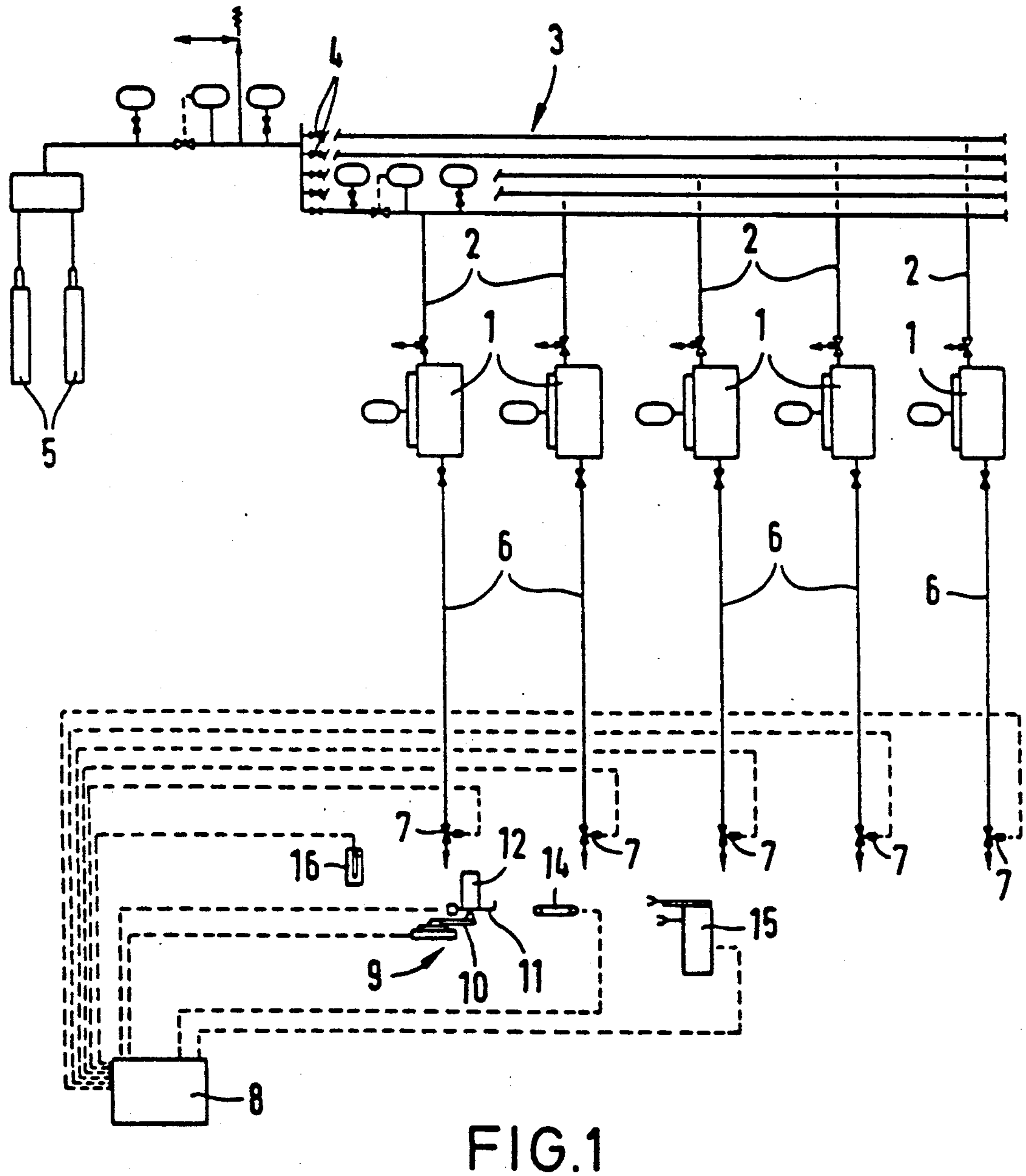
FIG. 1 is a flow chart of a plant or perfume factory of one embodiment of the invention.

As shown in FIG. 1, in one embodiment of the invention, a fully automatic perfume factory or plant for dosing and mixing perfumes comprises a plurality of reservoirs 1 for storing different perfumes, only a few reservoirs being shown by way of example in the drawing. These reservoirs 1 are connected by lines 2 to an inert gas system 3, from which inert gas can be fed under variable pressure through valves 4, from inert gas containers 5 to the reservoirs 1. A constant pressure level is established in the reservoirs 1 by the inert gas cushion provided by the gas, such as nitrogen, for example.

Each reservoir 1 is connected by a line 6 to an electrically controlled outlet dosing valve 7. Each valve 7 is connected to and actuated by a control computer 8. In this manner, the valves 7 are computer controlled.

Figure 2:
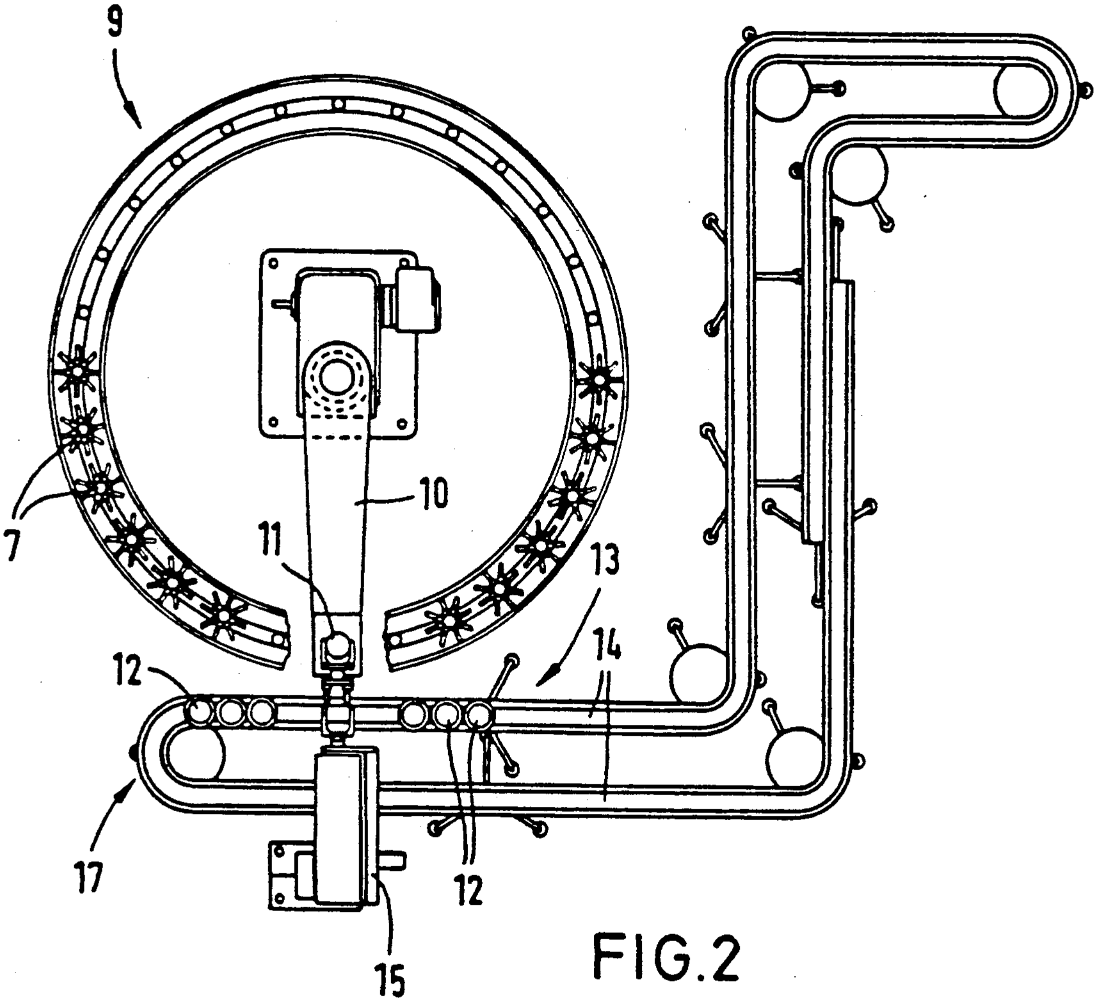
FIG. 2 is a plan view of a line of mixing vessels in one embodiment of the invention.

With references to FIG. 2, the individual outlet dosing valves 7 are preferably arranged in a circle 9 in a horizontal plane higher than that of the the juxtaposed line of mixing vessels 12 on conveyor 14. The mixing vessels 12 are successively and individually positioned on a weighing unit 11 on the outer end of turntable or rotatable arm 10, as described below. Rotatable arm 10 moves weighing unit 11, and an associated mixing vessel 12 in a circle under the circle of mixing valves 7, as will be described in greater detail below.

The line of mixing vessels 12 is preceded by a storage area 13 on conveyor belt 14 for mixing vessels 12 waiting to be filled. A handling unit 15 is used to transfer a mixing vessel 12 from the store 13 to the weighing unit 11 of the turntable or rotatable arm 10, at a loading/unloading position. The handling device 15 may be preceded by a scanner 16 which is designed to read codes on the mixing vessels 12 for the desired perfume mixtures as the latter moves towards the loading/unloading position. Scanner 16 is connected to the control computer 8.

The line of mixing vessels 12 is followed by another storage area 17 for filled mixing vessels 12 individually transported by the handling unit 15 onto conveyor 14. In the embodiment shown in FIG. 2, the first storage area 13 on the conveyor belt 14 is designed to circulate in such a way that after filling of mixing vessel 12, it becomes the second storage area 17 of mixing vessels on conveyor belt 14.

The dosing and mixing plant operation will now be described. First, a row of empty mixing vessels 12 arranged one behind the other is placed, for example, manually on the conveyor belt 14 in the storage area 13. The storage area 13 and/or mixing vessels 12 are provided with a code containing the desired mixture identification. The code on a mixing vessel 12 next to be used, is then read by the scanner 16 and fed into the control computer 8. Under the control of the computer, the handling unit 15 then takes up the particular mixing vessel 12 and transfers it from the conveyor belt 14 to the weighing unit 11 of the turntable 10. Depending on the desired mixture, the mixing vessel 12 is then moved via computer control under the circle 9 of dosing valves 7, by rotation of the turntable or arm 10 and brought under the particular outlet dosing valve 7 of the corresponding reservoir 1, where it is filled with the corresponding quantity of perfume by opening of the valve 7 and weighing by the weighing unit 11. In this manner, the turntable 10 successively moves the mixing vessel 12 under the necessary outlet dosing valves 7 of the particular reservoirs 1.

After one complete revolution of the turntable or arm 10 through 360°, the particular mixing vessel 12 now filled with the desired perfume formulation, is removed from the weighing unit 11 by the handling unit 15, and placed in the following storage area 17 of mixing vessels. To fill another mixing vessel 12, an empty mixing vessel 12 is again taken from the storage area 13 by the handling unit 15 and placed in the weighing unit 11 of the turntable or arm 10, and the process is repeated.

In summation of the preferred arrangement of apparatus and method of operation of the present perfume plant, further reference is made to FIGS. 1 and 2. Empty mixing vessels or containers 12 are placed successively on a generally L-shaped conveyor belt 14 in a storage area 13 before or upstream of a scanner 16. In this example, the conveyor belt moves in a counterclockwise direction, for moving each empty mixing vessel 12 past scanner 16. Scanner 16 reads coded information from each passing mixing vessel 12, and supplied a data signal to control computer 8 indicative of the perfume formulation associated with and to be dispensed into that particular container.

When such a mixing vessel 12 is moved via conveyor 14 to a loading/unloading position between handling unit 15 and weighing unit 11, computer 8 activates handling unit 15 to move the mixing vessel 12 onto the weighing unit 11. Note that the weighing unit 11 can be provided by conventional means. Also, the handling unit 15 can be provided by a conventional unit for moving individual containers 12 to and from the weighing unit 11.

Next, computer 8 activates turntable to rotate through 360°, and in doing so, to successively stop for positioning the mixing vessel on weighing unit 11 under an outlet dosing valve 7 associated with a reservoir 1 containing a necessary component of the perfume formula associated with the mixing vessel 12. The control computer 8 opens the associated valve 7 to dispense the required quantity of perfume component into the mixing vessel 12. Weighing unit 11 provides signals to the computer 8 indicative of the weight of mixing vessel 12 at any given time, for detecting when the necessary amount of perfume component has been received.

Control computer 8 then rotates turntable 10 to position mixing vessel 12 beneath the next dosing valve 7 associated with the next perfume component to be dispensed into mixing vessel 12. This process is continued until the mixing vessel 12 is so rotated through 360° and returned to its starting position, but now the mixing vessel is filled with various components necessary for its associated perfume formulation.

Control computer 8 activates handling unit 15 to remove the filled mixing vessel 12 from weighing unit 11, back onto conveyor belt 14. The computer 8 then activates conveyor 14 to move the filled mixing vessel 12 to a storage area 17 for filled ones of mixing vessels 12. Also, a new empty mixing vessel 12 is similarly moved into position between weighing unit 11 and handling unit 15, and the process is repeated for filling the new mixing vessel 12 with components necessary to its associated perfume formulation.

The invention is not confined to the embodiments shown by way of example in the drawing. Further embodiments of the invention are possible without departing from the basic concept. In particular, the configuration of the line of mixing vessels and the corresponding arrangement of the outlet dosing valves may be different. In addition, the central control computer may be accompanied by further operating computers for quasimanual intervention in the operation of the plant.

We claim:

1. A perfume processing plant for mixing predetermined doses of different substances to produce desired perfume formulations, said plant comprising:
   - a computer for controlling said processing plant;
   - a plurality of containers each for holding a different substance that may be included in a selected perfume formulation;
   - a plurality of dosing valves arranged in a circle and associated with individual ones of said plurality of containers, respectively;

a weighing unit for receiving a mixing vessel and for sending a signal to said computer indicative of the weight of said mixing vessel and its content;

an elongated rotatable arm including said weighing unit mounted on an outward end of said arm, an inward end of said arm being mounted for rotation at the center of said circle of dosing valves, said rotatable arm being controlled by said computer for movement in a circle for positioning said mixing vessel under selected ones of said dosing valves in a successive manner;

a conveyor belt having at least one portion thereof substantially tangential to one outside circumferential portion of said circle of dosing valves at a loading/unloading position;

a handling unit positioned on the opposite side of said conveyor belt to said circle of dosing valves, proximate said one portion of said conveyor belt;

a plurality of mixing vessels, said mixing vessels initially being empty and placed in juxtaposition on a first storage area of said conveyor belt;

said computer being programmed for in a sequential manner (1) operating said conveyor belt to position an empty one of said mixing vessels between said rotatable arm and said handling unit, (2) operating said handling unit to move said one mixing vessel from said conveyor belt onto said weighing unit on said rotatable arm, (3) rotating said arm to position said one mixing vessel for a given period of time proximate and under different selected ones of said dosing valves, respectively, (4) operating said dosing valves at appropriate times for discharging a predetermined quantity of an associated substance into said one mixing vessel, said computer being responsive to said weighing unit for controlling the quantity of a substance being dispensed, (5) after filling said one mixing vessel with appropriate quantities of said substances for obtaining a given perfume formulation, rotating said arm to move said one mixing vessel proximate said conveyor belt at said loading/unloading position, (6) operating said handling unit to move said one mixing vessel from said weighing unit back onto said conveyor belt, (7) operating said conveyor belt to both move said one mixing vessel to a second storage area of said conveyor belt for filled mixing vessels, and to move another empty one of said mixing vessels to said loading/unloading position, and (8) repeating said processing until a desired number of mixing vessels have been filled with preselected perfume formulations.

2. The perfume processing plant of claim 1, further including a machine readable code placed on each one of said plurality of mixing vessels for designating a desired perfume formulation, respectively, and a scanner positioned proximate the front end of said first storage area of said conveyor belt, for reading into said computer the coded information from the next one of said mixing vessels to be filled.

3. The perfume processing plant of claim 1, further including means for feeding an inert gas under variable pressure into each one of said containers, for maintaining a substantially constant pressure therein.

4. The perfume processing plant of claim 1, wherein said conveyor belt is generally L-shaped including a first leg substantially perpendicular to a second leg, said at least one portion being on an inside segment of said first leg.

5. The perfume processing plant of claim 4, wherein said second leg of said conveyor belt has a portion of an inside segment thereof adjacent another outside circumferential portion of said circle of dosing valves.

* * * * *